United States Patent [19]

Yeung et al.

[11] Patent Number: 4,921,348

[45] Date of Patent: May 1, 1990

[54] METHOD AND MEANS FOR A SPATIAL AND TEMPORAL PROBE FOR LASER-GENERATED PLUMES BASED ON DENSITY GRADIENTS

[75] Inventors: Edward S. Yeung, Ames, Iowa; Guoying Chen, Laramie, Wyo.

[73] Assignee: Iowa State University Research Foundation, Inc., Ames, Iowa

[21] Appl. No.: 301,485

[22] Filed: Jan. 26, 1989

[51] Int. Cl.$^5$ ............................................. G01N 21/41
[52] U.S. Cl. ..................................... 356/128; 356/432
[58] Field of Search .................. 356/432 T, 128, 129, 356/36; 219/121.62; 73/863.11

[56] References Cited

U.S. PATENT DOCUMENTS

| | | | |
|---|---|---|---|
| 4,299,494 | 11/1981 | Bado et al. | 356/432 |
| 4,468,136 | 8/1984 | Murphy et al. | 374/45 |
| 4,540,285 | 9/1985 | Amer | 356/432 |
| 4,543,386 | 9/1985 | Rose | 250/492.1 |
| 4,579,463 | 4/1986 | Rosencwaig et al. | 374/57 |
| 4,589,783 | 5/1986 | Thomas et al. | 374/45 |
| 4,591,272 | 5/1986 | Morris et al. | 356/432 |
| 4,591,718 | 5/1986 | Amer | 250/339 |
| 4,632,561 | 12/1986 | Rosencwaig et al. | 356/432 T |
| 4,634,290 | 1/1987 | Rosencwaig et al. | 374/5 |
| 4,636,088 | 1/1987 | Rosencwaig et al. | 374/5 |
| 4,750,822 | 6/1988 | Rosencwaig et al. | 356/432 T |
| 4,784,494 | 11/1988 | Pawliszyn | 356/432 T |
| 4,790,664 | 12/1988 | Saito et al. | 356/432 T |

OTHER PUBLICATIONS

Jackson et al, Photothermal Deflection Spectroscopy and Detection, *Applied Optics*, vol. 20, No. 8, Apr. 15, 1981, pp. 1333–1344.

"Measurement of the Electron Density Distribution in Plasmas from the Bending of a Gas Laser Beam", by Potter, et al., Journal of Physics E. (GB), vol. 5, No. 9 (Sep. 1972).

*Primary Examiner*—F. L. Evans
*Assistant Examiner*—Karen Paulette Hantis
*Attorney, Agent, or Firm*—Zarley, McKee, Thomte, Voorhees & Sease

[57] ABSTRACT

A method and means for a spatial and temporal probe for laser generated plumes based on density gradients includes generation of a plume of vaporized material from a surface by an energy source. The probe laser beam is positioned so that the plume passes through the probe laser beam. Movement of the probe laser beam caused by refraction from the density gradient of the plume is monitored. Spatial and temporal information, correlated to one another, is then derived.

23 Claims, 3 Drawing Sheets

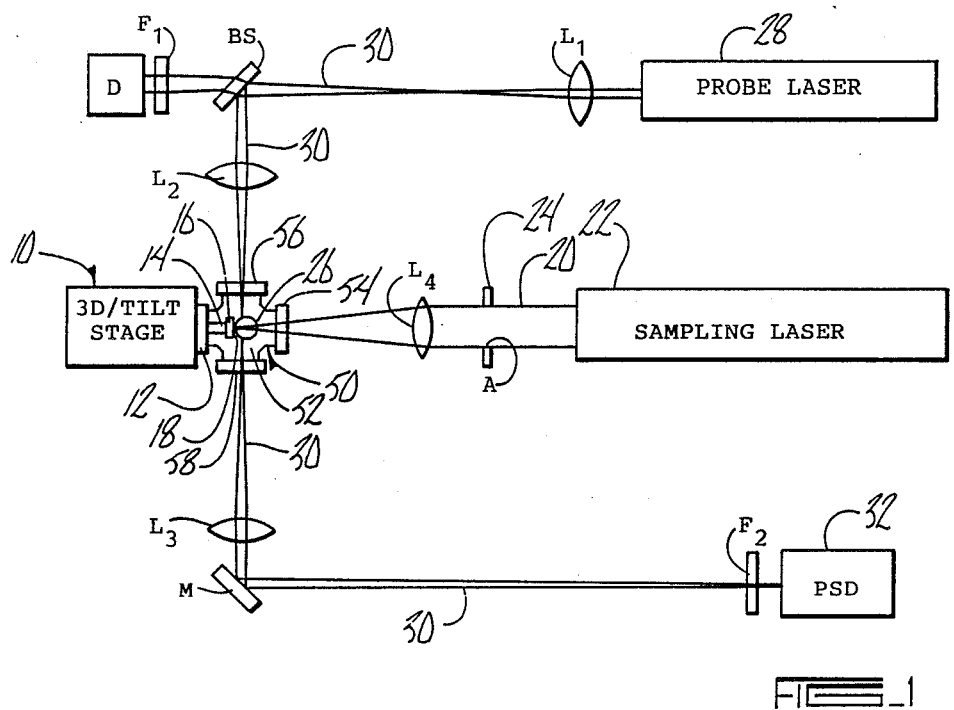
FIG_1
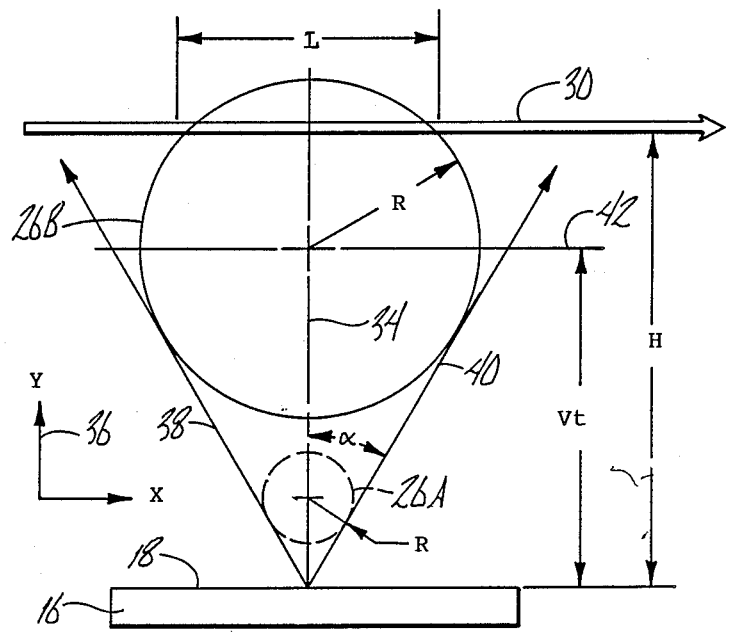
FIG_2

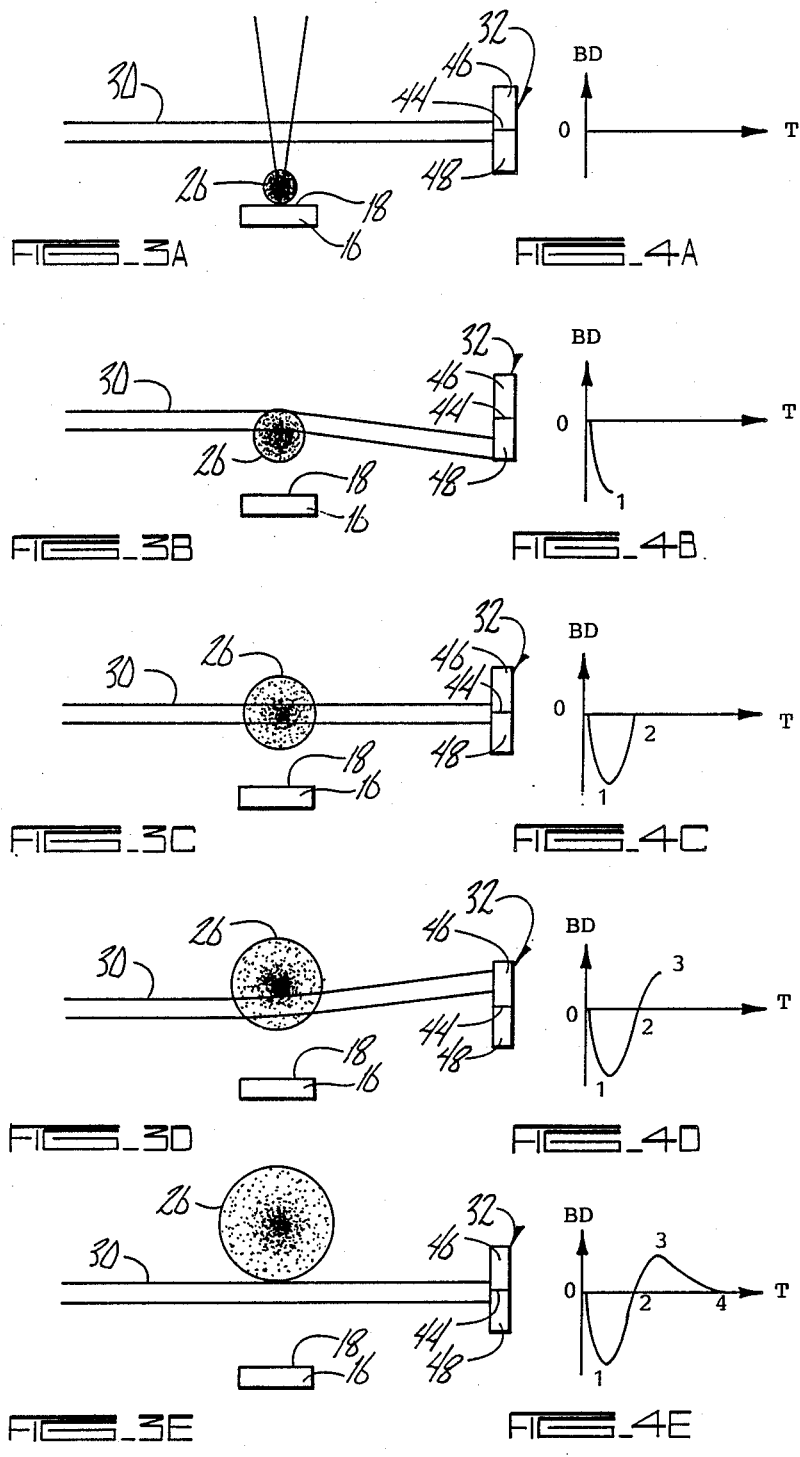

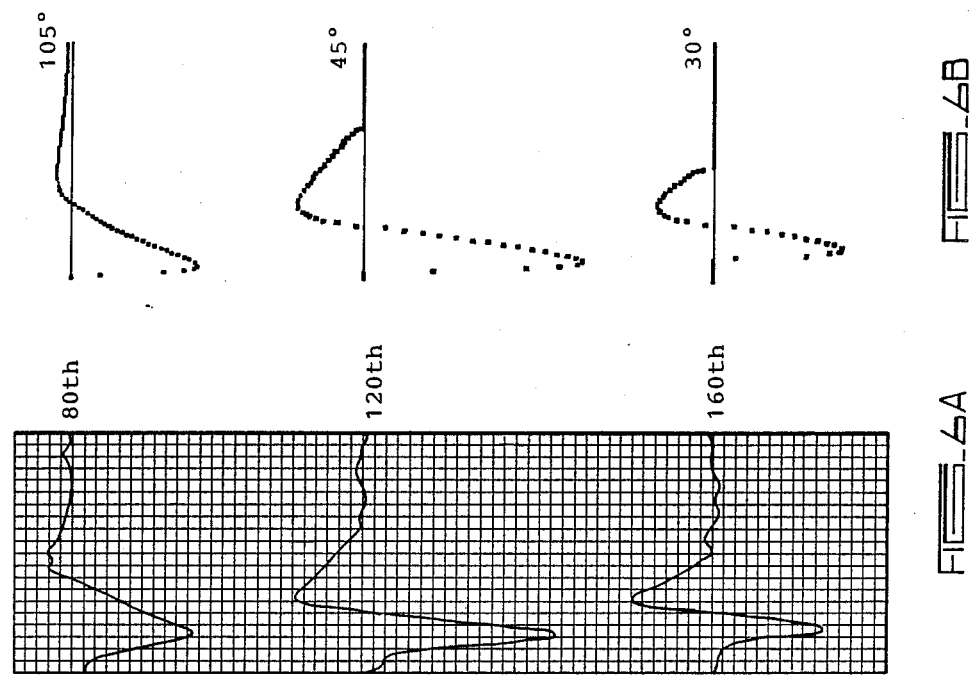
FIG. 6B
FIG. 6A
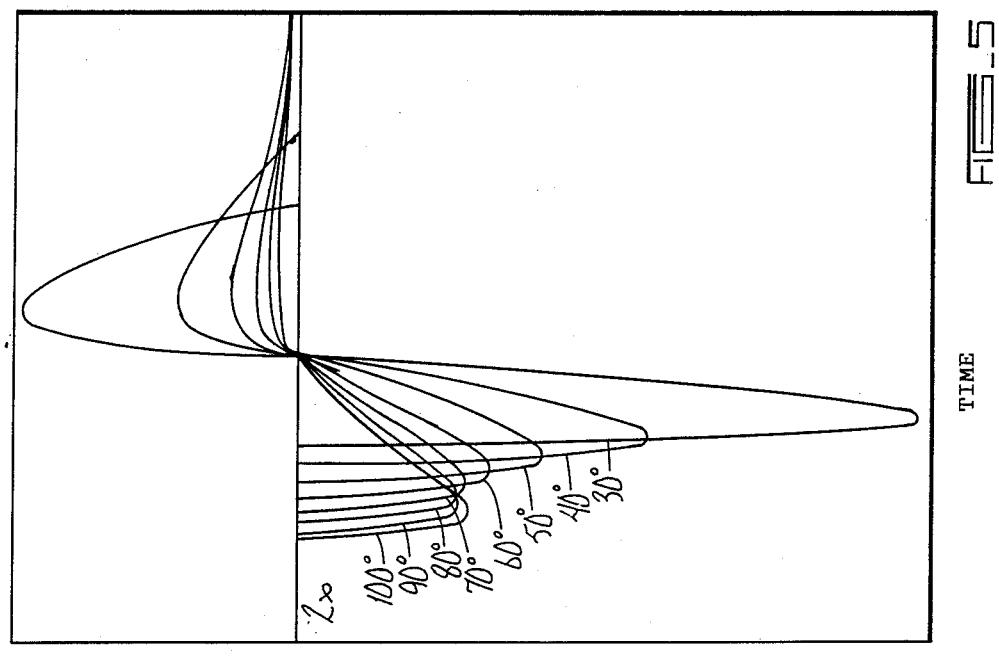
FIG. 5

METHOD AND MEANS FOR A SPATIAL AND TEMPORAL PROBE FOR LASER-GENERATED PLUMES BASED ON DENSITY GRADIENTS

This invention was made with Government support under Contract No. W-7405-ENG-82 awarded by the Department of Energy. The Government has certain rights in the invention.

BACKGROUND OF THE INVENTION (a) Field of the Invention

The present invention relates to analytical procedures regarding vaporization of materials by laser from a surface, and in particular, a probe for interrogation of laser-generated plumes having a density gradient.

(b) Problems in the Art

The imposition of an energy source, such as a laser beam, to a surface, with subsequent vaporization of a material on the surface, is of active interest for analytical purposes. The vaporized material forms what is called a plume, which generally expands and travels upwardly and away from the surface.

There are a number of techniques which can be used to analyze the plume of vaporized material. Some of these techniques are optical spectroscopy, mass spectroscopy, and interferometry.

These techniques are generally acceptable, but have shortcomings. Particularly with respect to use of a laser to generate the plume, these techniques are deficient in that they are not able to or are imprecise in deriving information about what occurs at the surface, and what occurs shortly after generation of the plume. Additionally, the results are unreliable. Some of the unreliability involves the inherent pulse fluctuations of laser beams, and varying surface properties of materials.

The benefit of more precise and reliable interrogation and derivation of information is important with respect to analysis of the surface and the vaporized materials, and can be helpful in analyzing material processing. One example would be the direct hard wiring of semiconductor devices.

Certain attempts have been made to improve over conventional methods. However, while some of these methods function adequately in certain situations, but not in others.

There is therefore a real need in the art for a universal probe which can be utilized in all different types of relevant situations.

It is therefore a principal object of the present invention to provide a method and means for a spatial and temporal probe for laser-generated plumes based on density gradients which improves over or solves the problems and deficiencies in the art.

A further object of the present invention is to provide a means and method as above described which is more precise and more sensitive than current techniques.

A further object of the present invention is to provide a means and method as above described which is useful in many types of interrogation of laser generated plumes.

Another object of the present invention is to provide a means and method as above described which provides correlated information regarding space and time with respect to the plume.

A further object of the present invention is to provide a means and method as above described which is efficient, economical, and accurate.

These and other objects, features, and advantages of the present invention will become more apparent with reference to the accompanying specification and claims.

SUMMARY OF THE INVENTION

The present invention is a method and means for a spatial and temporal probe for laser-generated plumes based on density gradients. A probe laser beam is oriented so that a plume generated by another energy source passes through the probe laser. The plume has a density gradient which has a refractive index. The probe laser is refracted according to the refractive properties of different parts of the density gradient of the plume as it moves through the probe laser. This movement of the probe laser, caused by refraction, is monitored. A position sensitive detector can be utilized for this purpose.

By utilizing this technique, sensitivity is enhanced and represents an improvement over the present state of the art. Because spatial and temporal information is correlated for each plume, information can be also derived about the material and surface from which the material is vaporized, which is not possible or which is not as accurate with presently utilized methods.

BRIEF DESCRIPTION OF THE DRAWINGS

FIG. 1 is a schematic of one embodiment of a system for a spa temporal probe for laser-generated plumes based on density gradients, according to the invention.

FIG. 2 is a schematic depiction of a generated plume relative to a surface and a probe beam.

FIGS. 3A-E are schematic representations of a generated plume and its upon a probe beam.

FIGS. 4A-E include graphic depictions of a signal generated from monitoring the probe beam corresponding to FIGS. 3A-E.

FIG. 5 is a graphic depiction of a beam deflection signal relative to time for different angles of expansion for the plume.

FIG. 6A is a graphic representation of three different beam deflection signals for different plumes.

FIG. 6B is graphic representations of the three plotted signals of FIG. 6A according to theoretical approximations.

DETAILED DESCRIPTION OF THE PREFERRED EMBODIMENT

With reference to the drawings, and particularly FIG. 1, there is shown a preferred embodiment of the present invention, in schematic form. Elements of the figures are identified by reference numbers. Like parts in all of the drawings will be identified by like reference numerals unless otherwise noted.

In FIG. 1, there is shown a three-dimensional or 3D/tilt stage 10, such as is known in the art, which has a base 12 including a mount 14 to hold a plate 16 having a top surface 18. Stage 10 includes means to precisely position mount 14 with respect to any direction or orientation. As can be seen in FIG. 1, mount 14 is oriented so as to hold plate 16 generally perpendicularly to and in line with sampling laser beam 20.

A sampling laser 22 generates sampling laser beam 20. Sampling laser beam 20 is first sent through aperture A in member 24. It is then focused onto the surface of sample plate 16 by lens $L_4$. In the preferred embodiment lens $L_4$ is a 7.5 centimeter focal length (f) UV grade planoconvex quartz lens.

Sampling laser 22, in the preferred embodiment, is a Model Hyper Ex 460 Excimer Laser available from Lumonics, in Ottawa, Canada. Laser 22 is operated at the 308 nanometer (nm) Xe Cl transition. Laser 22 is pulsed at a sampling rate of under 2 hertz (Hz) with a duration of each pulse typically 25 nano seconds (ns), with an energy of 31 milli Joules (mJ). The energy used for sampling is adjusted by varying the diameter of aperture A and the voltage of a power supply (not shown) sufficient to power laser 22.

Operation of sampling laser 22 directed upon the surface 18 of plate 16 would cause vaporization of a small amount of material on surface 18. This vaporization would form a plume 26 which would initially be tightly clustered, but then expand radially in all directions as it moves outwardly from surface 18.

A probe laser 28 generates a probe laser beam 30. In the preferred embodiment, probe laser 28 is an HeNe laser available from Spectra-Physics, Mountain View, Calif., Model 248, and is operated at 632.8 nm. Also, because of output fluctuations, a double beam configuration, such as is known in the art, is generated by probe laser 28. Probe laser beam 30 is first passed through a planoconvex lens $L_1$, having a focal length of 4.6 cm, to produce a compact probe beam waist. This is desirable to insure high spatial resolution and sensitivity. Probe beam 30 is then directed to 50% beam splitter BS. One portion of beam 30 therefore passes through beam splitter BS to a 632.8 nm line filter $F_1$ and then into reference beam detector D. The other portion of probe beam 30 is reflected from beam splitter BS through planoconvex lens $L_2$ (focal length of 25 cm) past the front surface 18 of plate 16 of stage 10. It is to be understood that lenses $L_1$ and $L_2$ are separated approximately 170 cm apart and in combination function to configure probe laser beam 30 so that it has a highly compact probe beam waist right in front of surface 18, approximately 0.5 mm away from surface 18.

A portion of probe beam 30 passing by surface 18 is then passed through a still further planoconvex 25 cm focal length lens $L_3$ which directs probe beam 30 to mirror M which focuses probe beam 30 through 632.8 nm line filter $F_2$ into position sensing detector 32.

Reference beam detector D receives a portion of probe beam 30 passing through beam splitter BS and monitors that portion. Detector D in the preferred embodiment is a photomultiplier tube available from Hamamatsu, Jersey, and is a Model R928. By utilizing a pin hole in front of detector D and filter $F_1$, detector D monitors whether probe laser 28 is outputting a 632.8 nm probe beam, and that combination minimizes any stray light from effecting such detection monitoring.

A pin hole and filter $F_2$ also serve to minimize stray light into position sensing detector 32, and to insure that the correct wavelength of probe laser 28 is being received. Position sensing detector 32 functions by monitoring any change in received position of probe laser beam 30. In other words, because plume 26 will generally refract probe beam 30, its point of incidence on position sensing detector 32 will change as the refractive index of plume 26 differs through its cross-section because of a density gradient. Position sensing detector 32 will output a signal correlated to the received position of probe beam 30 relevant to a reference point.

FIG. 2 schematically depicts the dynamics of a laser-generated plume 26. Sampling laser beam 20 is directed along line 34, which is parallel to the Y axis 36 normal to surface 18 of plate 16. Plume 26 is depicted as basically circular in cross-section (or spherical in three dimensions) and travels up and away from surface 18 along line 34. As it travels upwardly, its diameter expands somewhat geometrically. As shown in FIG. 2, lines 38 and 40 define an angle of expansion for plume 26 which is alternatively defined by two times angle $\alpha$, which is the angle between line 34 and either line 38 or line 40.

FIG. 2 depicts plume 26 in an early stage (see reference numeral 26A), and later in an expanded form (see reference numeral 26B). The radius of plume 26 is denoted by R. The center of plume 26 is denoted by Vt, which is the changing distance between the surface 18, and line 42 which intersects the center of plume 26 perpendicular to line 34. Additionally, reference letter H indicates the height from surface 18 to probe laser beam 30. Reference letter L depicts the linear distance of probe laser beam 30 through plume 26.

It is to be understood that plume 26, generated by sampling laser beam 20, is vaporized material from surface 18, and has a density gradient. As depicted in FIGS. 3A-E, plume 26 is generally compact with a more uniform density gradient just after generation, as shown in FIG. 3A. Plume 26 expands and travels upwardly to intersect probe beam 30, as shown in FIG. 3B, and has a greater density in its center than its perimeter. FIG. 3C shows further expansion and upward travel through probe beam 30, and its changing density gradient; as does FIG. 3D. FIG. 3E shows where plume 26 is completely passed through probe laser 30.

FIGS. 3A through 3E further depict the operation of position sensing detector 32. In the preferred embodiment, position sensing detector 32 can be a bicell photodiode detector, available from United Detector Technology, Hawthorne, Calif., Model PIN SPOT 2D, having a 6.5 mm² sensing area. Alternatively, a knife-edge/PMT (photomultiplier tube), Model No. R928 can be used. As is schematically depicted, in FIGS. 3A-E, position sensing detector 32 includes a centerline 44 dividing opposite sides 46 and 48. In its normal state (see FIG. 3A) probe beam 30 is adjusted so that it strikes both sides of centerline 44. As plume 26 first strikes probe beam 30, beam 30 is refracted towards the density gradient which moves the received beam 30 at position sensing detector 32 to side 48. Position sensing detector 32 then emits a signal indicating that probe beam 30 is being received at side 48 of sensing detector 32.

When plume 26 is centered in probe beam 30, even though beam 30 passes through the densest portion of plume 26, it is received by sensing detector 32 directly on either side of center line 44. Thus, no signal is produced by sensing detector 32. Then, as shown in FIG. 3D, once the center of plume 26 passes from probe beam 30, beam 30 is refracted, again towards the density gradient which causes sensing detector 32 to receive it at side 46. A distinct signal indicating its reception on side 46 is then generated by sensing detector 32. Finally, as shown in FIG. 3E, when plume 26 has passed completely through probe beam 30, it is again received on and around centerline 44 of detector 32, and no signal is produced.

FIGS. 4A-E depict a graphic representation of the signal produced by sensing detector 32 for situations set forth in FIGS. 3A-E. For purposes of reference, FIGS. 3A-E represent times T=0, 1, 2, 3, and 4. Thus, the plots of FIGS. 4A-E represent beam deflection as monitored by position sensing detector 32 as a function of time. In FIG. 4A, representing T=0, sample laser beam 20 has just created plume 26, which has not yet moved into probe beam 30, FIG. 4A thus shows only the axis of the graph. In FIG. 4B, representing T=1, plume 26 has just moved into probe beam 30 and has gradually deflected, by refraction, probe beam 30 to side 48 of sensing detector 32. An appropriate signal is generated and depicted in FIG. 4B, showing an increasing beam deflection up to T=1.

In FIG. 4C, it can be seen that the refractive properties of plume 26 are such that plume 26 is moved so that it is directly in the middle of probe beam 30. Thus, the signal from position sensing detector 32 shows decreasing beam deflection up to time T=2.

In FIG. 4D, plume 26 is passing out of probe beam 30, and shows the deflection of probe beam 30 to side 46 of detector 32, in an increasing amount up to time T=3. Once plume 26 passes completely out of probe beam 30, FIG. 4E shows decreasing deflection until probe beam 30 is again centered on detector 32.

It can be seen that between T=0 and T=4, plume 26 expands leaving a dense center with a decreasing-in-density radius to the perimeter. As indicated by FIG. 4E, it takes increased time for plume 26 to pass out of probe beam 30 because of its expanded state. Additionally, its density gradient is less in its outer perimeter and expanded state which results in less beam deflection. By understanding the signal shown in FIGS. 4A-E, understanding of plume 26 can be achieved, recognition of spatial information, such as the front, middle, and trailing portion of plume 26 can be derived, and since all this information is correlated with time, temporal information is also preserved and correlated.

Operation of the preferred embodiment of the invention can be achieved as follows. With reference to FIG. 1, plate 16 is a solid sample comprised of a ¼ inch by ¼ inch piece of 0.5 mm thick small P-type single crystal silicon wafer with resistively of 5.5-9.3 ohm-cm, available from SEH America, Vancouver, Wash. Mount 14 is a ¼ inch glass rod adjustably secured to base 12 of stage 10. Plate 16 can be attached to glass rod mount 14 by epoxy. Plate 16 and glass rod mount 14 are then completely and sealingly contained within a cell 50. Air is evacuated from cell 50 by connection to a two-stage glass diffusion pump to create a vacuum chamber 52 inside of cell 50. Windows 54, 56 and 58 allow sampling beam 20 and probe beam 30 to enter cell 50, and exit if necessary. Stage 10 is a tilt/3-D translational micrometer stage which can either be fabricated, as is within the skill of those of ordinary skill in the art, or purchased from vendors.

All of the elements of FIG. 1 are therefore adjusted and calibrated so that they will function accurately. For example, because accurate alignment of sampling beam 20 and probe beam 30 is necessary for high sensitivity of the invention, a microscope slide is first put in the position of plate 16. Sampling laser 22 is operated to pulse a sampling laser beam 20 onto the slide creating a small crater. Probe laser beam 30 is then aligned across the crater by utilizing a magnifying glass.

To further prepare the invention for operation and to maximize results, noise reduction is accomplished by minimizing mechanical vibrations. All optical components are mounted as rigidly as possible on a four foot by six foot optical table available from Newport of Fountain Valley, Calif., Model NRCXS-46, which is padded with a sheet of ⅛ inch thick rubber. Additionally, any mechanical pumps are paddle with one inch to two inch thick foam plastic sheets to absorb vibrations. Additionally, probe laser 28, because it is an excimer laser, is mounted on a separate support independent of the optical table.

To reduce air turbulence as a source of interference, the entire beam path for probe laser beam 30 can be shielded with one inch glass tubing with the ends of the tubing sealed with pin holes having a diameter slightly larger than the diameter of probe beam 30. Any equipment generating heat and air flow, such as power supplies and an oscilloscope, are located as far away from the optical table as possible. Finally, to enhance stable operation, probe laser 28 is warmed up for a time period before data is taken.

The output from the reference beam portion of probe 30, and position sensing detector 32 are, in the preferred embodiment, directed to an oscilloscope (for example, an oscilloscope made by Tektronix of Beaverton, Oreg., Model 7704A), including a differential amplifier module, Model 7A22 by Tektronix. Additionally, a Tektronix oscilloscope camera can be utilized to make selected hard copy visual records of the screen display of the oscilloscope (not shown). By pulsing sampling laser 22 upon plate 16, plume 26 is generated. It is to be understood that in the preferred embodiment UV radiation for sampling laser beam 20 is utilized because it couples better with most solid sample surfaces which means that efficient vaporization can be achieved even under relatively mild irradiation conditions. In the preferred embodiment, the energy used for sampling laser beam 20 was monitored by using an energy ratiometer (available from Laser Precision, Utica, N.Y., Model RRj7200) with an energy probe, available from Laser Precision, Utica, N.Y., Model RjP 734). The typical power density used for sampling laser beam 20 was below $10^9$ W/cm$^2$.

It was determined the knife edge/PMT position sensing detector was much more sensitive than the bicell photodiode detector because its high output current made amplifier noise negligible. In the preferred embodiment, a micrometer translation stage (not shown) was utilized to mount either bicell detector or knife edge detector to insure fine alignment. Typically, the position of the knife-edge detector was such that 50% intensity was registered by the photomultiplier tube of the detector. This meant that the intense HaNe probe laser beam 30 center was located right on the knife-edge position and maximum sensitivity could be obtained.

The average amount of material removed from plate 16 by each sampling laser beam shot was measured by weight difference before and after laser vaporization. To reduce any weighing error, the sample plate 16 was exposed to more than 10,000 laser pulses over different spots, with 170 to 180 exposures in each spot. A program written in Microsoft BASIC version 2.0 and run on an Apple Macintosh computer with 512K Ram on board was utilized to compute these averages. Additionally, photomicrographs of each crater was obtained from a metallurgical microscope available from Olympus, Lake Success, N.Y., Model BHM with a pm./10AD camera.

The theory of the invention can briefly be described as follows. Because plume 26 has a refractive index, it is known that the refractive index of a gaseous medium with "i" components is given by the Gradstone-Dale formula:

$$n - 1 = \sum_i k_i N_i \quad (1)$$

where n is the refractive index of the mixture; $N_i$ is the number density of the i-th component; and $k_i$ is the specific refractivity of the i-th component.

It is furthermore known in the art that the propagation of a Gaussian beam through a medium with spatially varying index of refraction is described by the paraxial equation:

$$\frac{d}{ds}\left(n_0 \frac{dr_0}{ds}\right) = \nabla n_{(r,t)} \quad (2)$$

where s is the light path, $r_0$ is the perpendicular displacement of the beam from its original direction, $n_0$ is the uniform index of refraction, and $n_{(r,t)}$ is the gradient of the index of refraction perpendicular to the light path.

Because the generation of a plume by laser is a highly violent process with a short time duration, it must be understood that the dynamics of the plume are simplified by certain assumptions. First of all, it is assumed that plume generation is instantaneous. This represents a fairly good approximation when the duration of the laser pulse used to create the plume is much shorter than the time of interception of the probe beam with the plume. Secondly, it is assumed that complete vaporization is achieved without generation of particles or clusters large enough to block the probe laser beam 30. This negates attenuation and refraction by large particles which would greatly complicate analysis of the results of the invention. This assumption can be validated by sampling under mild irradiation conditions with laser pulses of the appropriate wavelength.

Third, it is assumed that the wave length of the probe laser 28 is selected so that absorption and scattering by plume 26 can be neglected. This is satisfied by utilizing the 632.8 nm HeNe wavelength laser because the invention is probing collections of atoms. Fourth, it is assumed that atoms generated in the plume have uniform vertical velocity v leaving surface 18. It is to be understood that it was found that the mean squared ion velocity decreases proportionally with the square root of the peak intensity of the laser pulse for lower atomic weight materials. However, if pulse probe laser beam 30 is sufficiently focused onto a small enough area, so that the cross-sectional power density variations are effectively averaged out by rapid heat transfer, this assumption is valid. Fifth, it is assumed that atoms in the plume ejected are only subject to internal pressure, and that their radial expansion will be isotropic and linear. As depicted in FIG. 2, spherical plume 26 can then be described by its radius R and an angle of expansion $2\alpha$. If the invention is carried out under fairly low pressures, expansion of plume 26 is restricted within a cone, as has been discussed. See Irons, F. E.; McWhirter, R. W. B.; Peacock, N. J., J. Phys. B.: Atom. Molec. Phys. 1972, 5, 1975-1987.

Sixth, it is assumed that the density profile of plume 26 can be described by a radially linear function $$N^r = \left(1 - \frac{r}{R}\right)N^0 \quad (3)$$

where $N^r$ is the number density inside the plume at a distance r away from the center of the plume, and $N^0$ is the number density at the center of plume 26.

FIG. 2 depicts the dynamics of plume 26. Parameter vt is the vertical distance of the moving plume center with velocity v from the sample surface 18 at time t. The following equation quantifies these dynamics:

$$\frac{\partial \phi}{\partial x} = \frac{1}{n}\frac{\partial n}{\partial y} \quad (4)$$

The changing angle of deflection $\Delta \phi$ can be obtained by integrating the previous equation over the light path "l":

$$\Delta \phi = \int_0^L \frac{1}{n}\frac{\partial n}{\partial y} dx \quad (5)$$

Because all gaseous media have values of n very close to unity, especially when the amount of material vaporized is low, the 1/n factor can be moved out of the integral sign leading to the following result:

$$\Delta \phi = \frac{6 N_0 k (h - vt)}{\pi (vt \sin\alpha)^4} Ln \tan\left[\frac{1}{2}\arcsin\left(\frac{h - vt}{vt \sin\alpha}\right)\right] \quad (6)$$

where $N_0$ is the total number of atoms ejected in each laser pulse. From this expression, the angle of deflection can be calculated and compared to experimental results. Those experimental results are depicted in FIGS. 3A-E and 4A-E which show how the signal from a position sensing detector 32 is formed, basically by comparing the intensity from sides 46 and 48 of position sensing detector 32.

FIG. 5 depicts a graph of beam deflection signals (BD signals) from position sensitive detector 32 versus time for eight different plume angles of expansion $2\alpha$ (see FIG. 2). Probing height (H) is 0.05 cm, whereas vertical velocity of the plume equals 13900 cm./sec. As shown in FIG. 5, beginning with the left most curve the $2\alpha$ a angle is 100° and decreases by 10° for each succeeding curve, down to 30°. This graph shows how a larger expansion angle ($2\alpha$) produces a BD signal for a longer period of time but with less amplitude. As angle $2\alpha$ decreases, the BD signal narrows, corresponding to shorter time of interception of probe beam 30.

FIG. 6A shows graphic plots of the BD signal versus time from experimental procedures. Silicon plumes were generated under vacuum from the same spot on a silicon surface. FIG. 6A shows the plots for the 80th, 120th and 160th sample laser shots on the spot. This shows that early shots generated little plume material. Evaporation becomes more efficient after the surface is roughened. When the crater becomes deeper, the plume becomes more directional, i.e. the expansion angle decreases. At the 120th shot, maximum beam deflection was detected. Thus other information, besides time and space, can be derived.

FIG. 6B shows the theoretical results for the expansion angles of 105°, 45° and 30° respectively, and shows good agreement with actual results in FIG. 6A.

Using the embodiment of FIG. 1, it was discovered that the first few shots of probe laser beam 30 on the same spot on surface 18 of plate 16 created a beam deflection signal which was quite weak. The signal gradually increased in magnitude until approximately the 120th shot at the same spot; at which point the signal magnitude begins to decrease. It was further found that when the number of shots or exposures increased, the peak shape and magnitude of the deflection signal changed considerably. After about 250 exposures, the beam deflection signal decayed to zero.

It was further found that when position sensing detector 32 was bicell photodiode detector, it gave approximately linear response. By comparing beam deflection signals as depicted in FIGS. 4A-E and 6A, to the theoretical models previously described, it was determined that the embodiment of FIG. 1 correlated quite well with the theoretical predictions.

It is to be understood that when the expansion angle decreases, the beam deflection signal always narrows, corresponding to the shorter time of interception of probe beam 30.

It has been discovered that a smaller magnitude of beam deflection signal at the first successive laser vaporization exposures was caused because those first several shots generated little material on the "perfect" surface 18. As more shots hit surface 18, evaporation became more efficient because the surface was roughened. With more atoms removed, the crater becomes deeper and the expansion became more directional. At about the 120 shot, maximum beam deflection is observed because after that, the crater becomes so deep that focusing of the vaporization probe laser beam 30 changed considerably to decrease the power density, and it became more difficult for the atoms to escape.

It is also to be understood that contrary to some reports (see, e.g., David, C. E.; Avizonis, P. V.; Weichel, H.; Bruce, C.; Pyatt, K. D., IEEE, J. Quant. Electron. 1966-Qe-2, 493-499) which imply that laser generated plumes have constant radial density distribution in laser interferometry, it has been discovered that laser-generated plumes have a positive density gradient towards the plume center. As shown in FIGS. 3A-E and 4A-E, experimental results suggest that laser-generated plumes have a radially linear density distribution. Although the plume is very compact at the early stage of expansion, once expansion occurs, this density gradient is observable. It may be, however, that there is an even steeper density gradient towards the center which would lead to a more stable expansion.

It is further to be understood that when the probe beam 30 passes directly through the center of plume 26, it "sees" zero density gradient, regardless of any density pattern, as long as the density is symmetrical.

Furthermore, it was discovered that during operation, not all material leaves surface 18 as vapor. Some of the material forms a crater around the hole by deposition. It is estimated that 84% of the material initially in the hole escapes from the surface representing a highly efficient vaporization process.

Furthermore, it was confirmed that the invention works equally well irregardless of the nature of conditions of the material of plate 16.

By comparison to other methods, the present invention is advantageous for a number of reasons. Since it measures not bulk index refraction, but the gradient in one pass, it is especially suited to systems with dramatic temporal variations. It is also much easier to focus the probe beam 30 into spots within the tiny laser plume 26, which results in higher spatial resolution and higher sensitivity. It is approximated that the present invention has detection sensitivities of one nanogram (ng). Correlated spatial and temporal information are possible for individual laser vaporization events.

The included preferred embodiment is given by way of example only, not by way of limitation to the invention, which is solely described by the claims herein. Variations obvious to one skilled in the art will be included within the invention defined by the claims.

What is claimed is:

1. A method for deriving spatial and temporal information for laser-generated plumes having a density gradient, comprising:
   imposing a first energy source upon a material on a surface to generate a plume of vaporized material;
   passing a probe beam from a second energy source through the plume;
   detecting refraction of the probe beam as a function of the density gradient of the plume.

2. The method of claim 1 wherein the first energy source is generated by a laser.

3. The method of claim 2 wherein the laser generates a laser beam which is directed generally perpendicularly to the surface.

4. The method of claim 1 wherein the first energy source is focused onto a small area of the surface.

5. The method of claim 1 wherein the first energy source is pulsed upon the surface.

6. The method of claim 1 wherein the second energy source is generated from a second laser.

7. The method of claim 6 wherein the probe beam from the second laser is directed parallelly to the surface, at a spaced apart level from the surface.

8. The method of claim 1 wherein detecting refraction of the probe beam further comprises detecting movement of the probe beam as a result of refraction through the density gradient of the plume.

9. The method of claim 8 wherein detection of movement of the probe beam is accomplished by a position sensitive detector means.

10. The method of claim 1 further comprising generating a signal representing refraction of the probe beam as a function of the density gradient of the plume.

11. A method for deriving spatial and temporal information for laser-generated plumes having a density gradient comprising:
    creating a laser-generated plume of vaporized material from a surface;
    positioning a laser probe beam with respect to the surface so that the plume will pass through the probe beam;
    detecting the position of the probe beam prior to, during and after the plume passes through the probe beam.

12. A spatial and temporal probe for laser-generated plumes having a density gradient comprising:
    means for producing a laser-generated plume from a material on a surface;
    means for producing a probe laser beam;
    means for directing the probe laser beam to a set position above the surface so that any plume produced will pass through the probe laser beam;
    means for monitoring the refraction of the probe beam as a result of the density gradient of the plume as the plume moves through the probe laser beam.

13. The probe of claim 12 wherein the means for producing a laser-generated plume comprises a laser.

14. The probe of claim 13 wherein the laser is positioned so as to direct a laser beam generally perpendicularly to the surface.

15. The probe of claim 12 wherein the means for producing a probe laser beam comprises a second laser.

16. The probe of claim 15 wherein the second laser is positioned so as to direct the probe laser beam generally parallelly to the surface, at a spaced apart level from the surface.

17. The probe of claim 12 wherein the surface is enclosed in an air tight chamber to allow evacuation of air from the chamber, the chamber having window means allowing passage of energy from the means producing a laser generated plume and energy from the means for producing a probe laser beam.

18. The probe of claim 12 wherein the means for monitoring the refraction of the probe beam comprises a position sensitive detector means.

19. The probe of claim 18 wherein the position sensitive detector means monitors intensity and position of the probe laser beam.

20. The probe of claim 18 wherein the position sensitive detector means comprises a photomultiplier tube.

21. The probe of claim 18 wherein the position sensitive detector means comprises a bi-cell photo-diode detector.

22. The probe of claim 12 wherein the means for monitoring the refraction of the probe beam generates a signal from which density gradient of the plume can be derived and correlated to time.

23. The probe of claim 12 wherein the means for monitoring the refraction of the probe beam generates a signal from which density gradient of the plume can be derived and correlated to the total amount of matter vaporized in the plume.

* * * * *